United States Patent [19]
Bishop et al.

[11] Patent Number: 5,834,232
[45] Date of Patent: Nov. 10, 1998

[54] CROSS-LINKED GELATIN GELS AND METHODS OF MAKING THEM

[75] Inventors: Paul D. Bishop, Fall City; Gerald Lasser, Everett, both of Wash.

[73] Assignee: ZymoGenetics, Inc., Seattle, Wash.

[21] Appl. No.: 641,463

[22] Filed: May 1, 1996

[51] Int. Cl.$^6$ ............ C12P 21/06; C12N 11/04; C12N 9/10; A61K 38/17
[52] U.S. Cl. ............ 435/68.1; 435/182; 435/193; 530/354
[58] Field of Search ............ 435/68.1, 174, 435/177, 180, 182, 193; 530/356, 354

[56] References Cited

U.S. PATENT DOCUMENTS

| | | | |
|---|---|---|---|
| 3,619,236 | 11/1971 | Dappen et al. | 430/621 |
| 4,703,108 | 10/1987 | Silver et al. | 530/356 |
| 4,877,724 | 10/1989 | Chen et al. | 430/621 |
| 5,156,956 | 10/1992 | Motoki et al. | 435/68.1 |
| 5,169,631 | 12/1992 | Rase et al. | 424/401 |
| 5,514,579 | 5/1996 | O'Hara et al. | 435/352 |
| 5,567,806 | 10/1996 | Abdul-Malak et al. | 530/356 |

FOREIGN PATENT DOCUMENTS

| | | |
|---|---|---|
| 2 659 352 | 9/1991 | France . |
| 58-28295 | 2/1983 | Japan . |
| 06078783 | 3/1994 | Japan . |
| 6-98743 | 4/1994 | Japan . |
| 93/22930 | 11/1993 | WIPO . |

OTHER PUBLICATIONS

Mosher et al., "Cross-linking of collagen and fibronectin by factor XIIIa", J. Biol. Chem. (1980) 255(3), pp. 1181–1188, Feb. 1980.

Dickinson et al. "Rhealogy of milk protein gels and protein-stabilized emulsion gels cross-linked with transglutaminase", J. Agri. Food Chem. (1996) 44(6), pp. 491–495.

Djabourov et alk., *Bioreology 30*: 191–205, 1993.

Sakamoto et al., *Journal of Food Science 59(4)*: 866–871, 1994.

Soria et al., *Experientia 31(11)*: 1355–1357, 1975.

Paye et al., *European Journal of Cell Biology 45*: 44–50, 1987.

Akiba et al., *Graefe's Arch. Clin. Exp. Opthalmol. 231*: 408–412, 1993.

*Primary Examiner*—Jean C. Witz
*Assistant Examiner*—Susan Hanley
*Attorney, Agent, or Firm*—Gary E. Parker; Paul G. Lunn

[57] ABSTRACT

Enzymatically cross-linked protein gels and methods for preparing them are disclosed. The methods comprise adding a transglutaminase, such as factor XIII, to a composition of a temperature-sensitive gel-forming protein, such as gelatin or collagen, and incubating the composition and transglutaminase under gel-forming conditions. The resulting gels have superior strength and thermal stability, and can be used within a variety of medical and industrial applications.

28 Claims, 2 Drawing Sheets

CROSS-LINKED GELATIN GELS AND METHODS OF MAKING THEM

BACKGROUND OF THE INVENTION

Protein gels are used in a variety of applications in industry and medicine. For example, gelatin films are used for photographic emulsions. In the food industry, protein gels are components of processed fish products ("surimi"), candies, desserts, fat substitutes, soy products and milk products. See, for example, WIPO publication No. WO 93/22930; Japanese Patent Application Publication No. 5260893; and U.S. Pat. No. 5,420,025. In medicine, gels are used as delivery vehicles, such as gelatin capsules (e.g., published French Patent Application No. 3 659 352 A1) and vehicles for topical application of polypeptide or other drugs (e.g., U.S. Pat. No. 5,427,778). Gels are also used in cosmetic preparations.

Conventional protein gels often lack thermal stability, high strength, resistance to proteolysis after enzymatic cross-linking (McDonagh, J., in *Hemostasis and Thrombosis,* 2nd Ed., ed. C. Colman et al., J. B. Lippincot Co., Philadelphia, 1987), and elasticity, thus limiting their use. For example, conventional gelatin gels melt at about 28°–32° C., depending on protein concentration. This melting is reversible, with the solution converting back to the gel state upon lowering of the temperature. Concentration dependence of gelation and other properties of gelatin has been reported by Michon et al. (*Rheol. Acta.* 32:94–103, 1993).

Stabilization of gels can be achieved by cross-linking, either by chemical or enzymatic means. See, for example, Nastruzzi et al., *J. Microencapsulation* 11(3):249–260, 1994; Digenis et al., *J. Pharm. Sci.* 83(7):915–921, 1994; Shinde et al., *Bio-Medical Materials and Engineering* 2:123–126, 1992; van Washem et al., *J. Biomed. Mater. Res.* 28:353–363, 1994; Koide et al., *J. Biomed. Mater. Res.* 22:79–87, 1993; and Penhoat et al., *Biomaterials* 14(7):503–506, 1993. Enzymatic cross-linking of proteins in complex mixtures (food products) using transglutaminases has been reported (e.g., U.S. Pat. No. 4,917,904). Such methods, which involve incubation of enzyme-substrate mixtures at temperatures up to 90° C., are reported to improve food texture. Chemical cross-linking, such as with glutaraldehyde or carbodiimide, improves gel strength but produces an amorphous (non-uniform) gel. See, for example, Gerhart et al., *J. Biomed. Mater. Res.* 22(11):1071–1082, 1988; and Kaalem et al., *Nature* 325(6102):328–329, 1987. Chemical cross-linking agents are often toxic, immunogenic, and/or inflammatory, thereby limiting their use in the production of foodstuffs, medicaments, and cosmetics.

Gels are a thermodynamic state and, as such, their properties at equilibrium should be independent of the pathway taken for the liquid/gel phase transition. In practice, however, gel properties are dependent on the kinetics of gelation, and the kinetics are in turn a function of the pathway. Furthermore, it is possible to force molecules into a qualitatively different physical state though the use of crosslinking agents, such as chemical cross-linking agents and transglutaminases. For example, gelatin or other protein solutions can be crosslinked before they can naturally gel and/or under conditions where they would not otherwise gel at all (e.g., high temperature). Gelatin can thus be forced to form such networks (sometimes referred to as gels) at temperatures above its gel point. Although such cross-linking results in a reduction in solubility and an increase in working temperature, the resulting materials may have even less strength and elasticity than conventional gels, and native protein structure (and biological properties) may be lost.

There remains a need in the art for high-strength, uniform protein gels. There also remains a need for improved protein gels that are free of toxic agents. There is an additional need for protein gels with improved thermal stability. There is a further need for methods for incorporating additives, such as bioactive molecules, into gels. The present invention provides such improved gels and methods of making improved gels, as well as other, related advantages.

SUMMARY OF THE INVENTION

Within one aspect, the invention provides a method of preparing a cross-linked protein gel comprising the steps of (a) adding a transglutaminase to a composition of a temperature-sensitive gel-forming protein; and (b) incubating the composition and transglutaminase at a temperature at which a like composition lacking transglutaminase will gel, whereby the composition is converted to a cross-linked gel. Within one embodiment, the composition is in the form of an aqueous solution. Within an alternative embodiment, the composition is in the form of a gel. Within additional embodiments, the gel-forming protein is gelatin or collagen. Within other embodiments, the transglutaminase is selected from the group consisting of factor XIII, tissue transglutaminase, keratinocyte transglutaminase, epidermal transglutaminase, and prostate transglutaminase. The composition may further comprise one or more additional proteins selected from the group consisting of fibronectin, von Willebrand factor, vinculin, and laminin. The composition may also further comprise a cytokine or a hormone.

Within a second aspect of the invention there is provided a method of preparing a cross-linked protein gel comprising the steps of (a) forming an aqueous solution of a temperature-sensitive gel-forming protein, (b) adding transglutaminase to the solution in an amount sufficient to catalyze cross-linking of the temperature-sensitive gel-forming protein, and (c) incubating the transglutaminase-containing solution under conditions of time and temperature in which a like solution lacking transglutaminase will gel. Within a preferred embodiment, the aqueous solution is subjected to at least one cycle of gelation and melting before the addition of the transglutaminase. Within another embodiment, the protein is gelatin and the transglutaminase-containing solution is incubated at a temperature of from 4° C. to 33° C. Within other embodiments, the gel-forming protein is gelatin or collagen. Within an additional embodiment, the protein is gelatin, the gelatin concentration is from 1% to 10% by weight, and the transglutaminase-containing solution is incubated at a temperature of from 20° C. to 32° C. Within a further embodiment, the protein is gelatin, the transglutaminase is factor XIII, and the gelatin and factor XIII are present in a mass ratio of from 528:1 to 66:1. The transglutaminase-containing solution may further comprise one or more additional proteins selected from the group consisting of fibronectin, von Willebrand factor, vinculin, and laminin, preferably in an amount not exceeding 10% by weight of said gel. The transglutaminase-containing solution may also further comprise a cytokine or a hormone.

Within a third aspect of the invention there is provided a method of preparing a cross-linked protein gel comprising adding a transglutaminase to a protein gel, whereby the transglutaminase diffuses into the gel and catalyzes cross-linking of the protein.

Within a fourth aspect of the invention there is provided a cross-linked protein gel prepared according to one of the methods disclosed above. Within one embodiment, the gel is in the form of a pharmaceutical composition, such as a composition in which the gel provides a vehicle for an amine-containing drug, wherein the drug is cross-linked to the gel. Within a related embodiment, the gel is in the form of a microcapsule. Within another embodiment the gel is coated on a polymeric or paper support and may further comprise silver halide grains or a dye-forming coupler compound.

These and other aspects of the invention will become evident upon reference to the following detailed description and the attached drawings.

DETAILED DESCRIPTION OF THE INVENTION

Figure 1:
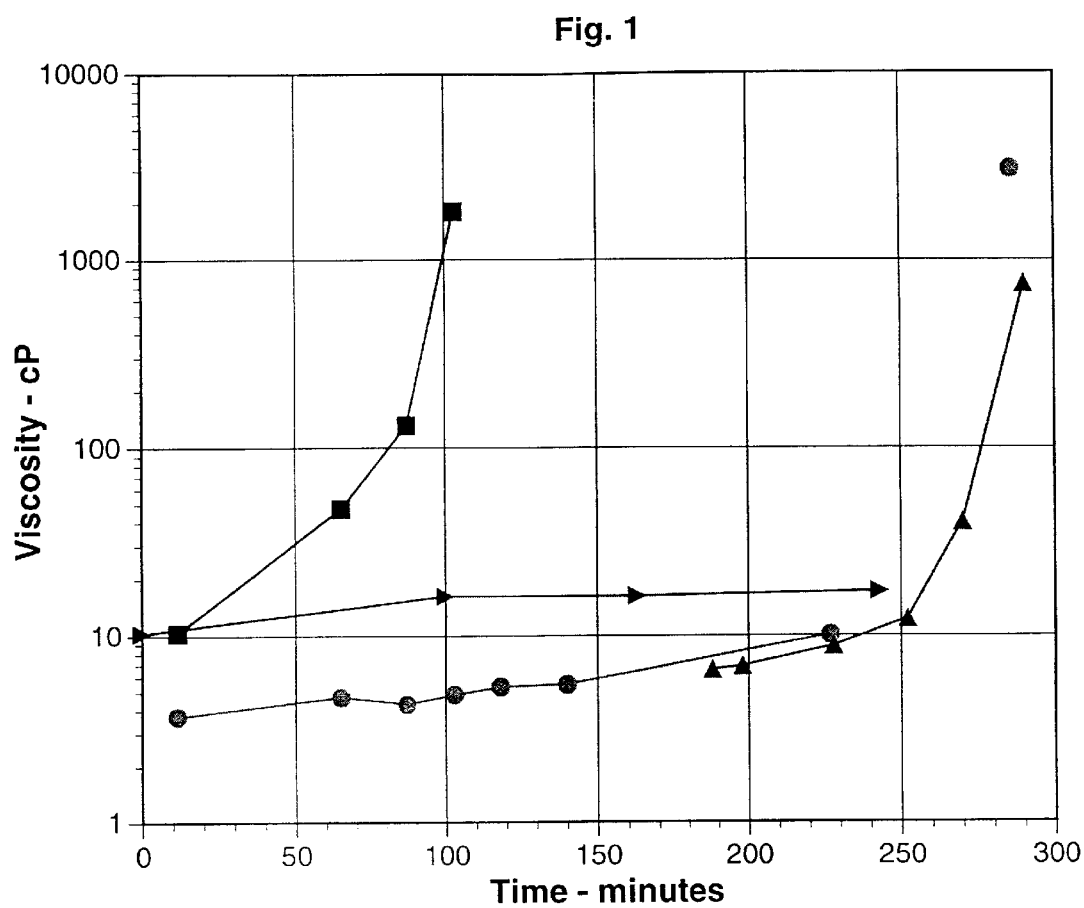
FIG. 1 illustrates changes in viscosity of gelatin gels prepared under various conditions as disclosed in Example 1.

The term "cross-linking" is used herein to denote the formation of covalent bonds between polymer chains to make a single network with increased strength and resistance to solvents. Transglutaminases catalyze the formation of γ-glutamyl ε-lysine isopeptide bonds.

As used herein, the term "factor XIII" includes the complete factor XIII zymogen tetramer ($A_2B_2$) and factor XIIIa ($A'2$ or $A'A$), as well as activation intermediates and subunits thereof, including $A'_2B_2$ and $AA'B_2$ intermediates, the A subunit, the A' subunit and $A_2$ dimers. The $A_2$ dimer, which is readily produced by recombinant methods or can be isolated from platelets and placenta, is a preferred form.

The term "gel" is used herein to denote a swollen, hydrated polymer network which is essentially continuous throughout its volume. A protein gel is composed of an essentially continuous network of linked protein molecules and a liquid (typically aqueous) solvent, which fills the space within the the protein matrix. The protein matrix exerts a strong viscous drag on the solvent molecules, preventing them from flowing freely. The component molecules making up the gel network may be linked by ionic, hydrophobic, metallic or covalent bonds. The covalent bond is the most thermally stable of these bonds.

The term "gel point" is used for the transition point between the fluid (sol) state and the gel state. The gel point can be observed as a sudden loss of fluidity as the material rapidly changes from a viscous liquid to an elastic material of infinite viscosity. This sudden, discontinuous transition in the viscosity of the fluid is marked by changes in physical characteristics; bubbles no longer rise in the material, and breaking strength and elastic modulus increase. At the gel point the molecular weight (weight average) of the protein matrix becomes "infinite", i.e., an essentially continuous matrix is formed throughout the nascent gel. Polymerization can continue beyond this point, incorporating more soluble protein into the matrix.

A "temperature-sensitive gel-forming protein" is a protein that gels in response to a change in temperature. These proteins have a definable gel point, the temperature at which gelation occurs. The gel point of a protein varies somewhat with protein concentration and other factors. Examples of temperature-sensitive gel-forming proteins include gelatin and collagen. Gelation of these proteins is discussed in more detail below. This definition specifically excludes proteins that form gel-like matrices in response to other physical changes, such as the formation of fibrin polymers upon proteolysis of fibrinogen. The term "temperature-sensitive protein gel" is used to denote gels formed from temperature-sensitive gel-forming proteins.

The present invention is based in part upon the discovery that enzymatically cross-linking protein gels during or subsequent to gelation results in gels having superior properties, including uniformity, strength, and thermal stability. According to the present invention improved gels are formed by enzymatically cross-linking protein compositions under conditions in which a like composition lacking cross-linking enzyme will gel. Thus, a transglutaminase is added to a composition of a temperature-sensitive gel-forming protein, such as gelatin or collagen, and the composition and transglutaminase are incubated at a temperature at which a like composition lacking transglutaminase will gel, whereby the composition is converted to a cross-linked gel. Within one embodiment of the invention, a solution of protein and transglutaminase is incubated at a temperature conducive to gel formation and for a time sufficient for gel formation. The inventors have found that enzymatic cross-linking under gel-forming conditions results in improved strength and thermal stability as compared to non-cross-linked gels or gels subjected to enzymatic cross-linking under sol-state conditions. For example, gelatin gels produced according to the methods of the present invention using factor XIII as the cross-linking enzyme are, on average, more than 2.5 times as strong as comparable gels prepared without factor XIII. Cross-linking stabilizes the higher order structure of protein gels, making them stable at temperatures above the melting point of otherwise similar, non-cross-linked gels. Such stabilization is also expected to make the cross-linked gels resistant to proteolysis in view of the known relationship between helical structure and protease resistance (see Raghunath et al., *J. Mol. Biol.* 236:940–949, 1994).

Experimental evidence also indicates that gels prepared according to the present invention are cross-linked primarily at native helix formation sites (i.e., adhesion sites that are zones of partially renatured helix). See, Ross-Murphy, *Polymer* 33: 2622–2627, 1992; and Stainsby, G., in *Food Polymers, Gels and Colloids*, ed. E. Dickinson, Royal Society of Chemistry, London, 1991. Cross-links produced by transglutaminases are contrasted to chemically-produced cross-links in that they selectively stabilize the collagen-like helix structure of adhesion zones. Transglutaminase cross-linking thereby provides for a more normal and uniform gel structure, whereas chemically cross-linked gels exhibit a more random pattern of cross-linking. While not wishing to be bound by theory, it is believed that the observed pattern of enzymatic cross-linking results from the formation of at least most of the cross-links after gelation has occurred.

Cross-linking of protein gels increases their thermal stability. However, melting of cross-linked gels is irreversible insofar as the improved properties are lost. The present inventors have discovered, however, that gelatin gels cross-linked with a representative transglutaminase, factor XIII, according to the methods of the present invention are stable to above 100° C. Thermal stability (melting temperature) of such gels is a function of degree of cross-linking, which can be controlled by adjusting the cross-linking time by, for example, thermal or chemical denaturation of the transglutaminase or by adding selective inhibitors prior to completion of cross-linking, or by adjusting the transglutaminase concentration.

Transglutaminases useful within the present invention include those produced by microorganisms and higher organisms. Mammalian transglutaminases, such as factor XIII (U.S. Pat. No. 5,204,447; European Patent No. 0 268 772), keratinocyte transglutaminase (Phillips et al., *Proc. Natl. Acad. Sci. USA* 87:9333–9337, 1990; Phillips et al., *Biochemistry* 32:11057–11063, 1993), tissue transglutaminase (WIPO Publication WO 92/12238), prostate transglutaminase (WIPO Publication WO 93/13207), and epidermal transglutaminase (WIPO Publication WO 91/06553; Folk, *Ann. Rev. Biochem.* 49:517–531, 1980), are preferred. Microbial transglutaminases (see, e.g., European Patent Office Publication 0 379 606 A1 and U.S. Pat. No. 5,420,025) can also be used, particularly in the preparation of food products. For medical uses, it is preferred to use a transglutaminase from the species to be treated so as to avoid complications due to immunogenicity. Medical products intended for use in humans are preferably made using a human transglutaminase, while veterinary products are prepared using an appropriate non-human transglutaminase.

Transglutaminases for use within the present invention are prepared according to known means, including microbial fermentation (U.S. Pat. No. 5,156,956), extraction from plasma or tissue (Cooke and Holbrook, *Biochem. J.* 141:79–84, 1974; Curtis and Lorand, *Methods Enzymol.* 45: 177–191, 1976; U.S. Pat. Nos. 3,904,751; 3,931,399; 4,597,899; 4,285,933; and 5,130,879), or recombinant production. Recombinant production (i.e., production using genetically engineered host cells) is preferred because it allows production of highly purified proteins uncontaminated by infectious agents and can be scaled up for commercial production. Methods for preparing recombinant transglutaminases are disclosed by, for example, Bishop et al., U.S. Pat. No. 5,204,447; Davie et al., EP 268,772; Grundmann et al., AU-A-69896/87; and WIPO Publications WO 91/06553, WO 92/12238, and WO 93/13207, which are incorporated herein by reference in their entirety.

It is preferred to produce factor XIII $A_2$ dimer cytoplasmically in yeast (*Saccharomyces cerevisiae*) using the method disclosed by Bishop et al. (*Biochemistry* 29: 1861–1869, 1990), in copending U.S. patent application Ser. No. 08/333,236, and in WIPO Publication WO 93/03147, which are incorporated herein by reference in their entirety. The cells are harvested and lysed, and a cleared lysate is prepared. The lysate is fractionated by anion exchange chromatography at neutral to slightly alkaline pH using a column of derivatized agarose, such as DEAE Fast-Flow Sepharose™ (Pharmacia) or the like. Factor XIII is then crystallized from the column eluate by concentrating the eluate and adjusting the pH to 5.2–5.5, such as by diafiltration against ammonium succinate buffer. The precipitate is then dissolved and further purified using conventional chromatographic techniques, such as gel filtration and hydrophobic interaction chromatography.

Temperature-sensitive gel-forming proteins that can be used within the present invention include gelatin, collagen, casein, whey proteins (e.g., alpha-lactalbumin), and synthetic polymers containing transglutaminase substrate sites (e.g., polymers disclosed in U.S. Pat. No. 5,428,014). Such synthetic polymers will generally comprise repeating polypeptide units, including transglutaminase substrate sites, such as the Leu-Ser-Gln-Ser-Lys sequence of β-casein (SEQ ID NO:1). Gels can also be formed between mixtures of temperature-sensitive gel-forming proteins. For example, the gelation of a heat-induced complex between K-casein and a-lactalbumin is disclosed by Doi et al. (*J. Nutr. Sci. Vitaminol.* (Tokyo) 31:77–87, 1985).

An exemplary protein for use in preparing a gel according to the present invention is gelatin. Gelatin is produced from collagen by acid (Type A) or alkaline (Type B) hydrolysis and thermal denaturation of the collagen fibers (Ross-Murphy, ibid.). With heating, the triple helix of the hydrolyzed collagen unfolds, and the protein becomes soluble. Cooling of the protein, now referred to as gelatin, causes a partial re-folding of the helix and results in a network of helical junctions. At a critical point determined by such factors as protein concentration, temperature, and ionic strength of the solvent, the network is extensive enough to form a gel. These gels are thermoreversible gels, and their properties have been extensively studied. See Michon et al. (ibid.) and references cited therein.

Those skilled in the art will recognize that the methods of the present invention can also be applied to other temperature-sensitive gel-forming proteins. A preferred such other temperature-sensitive gel-forming protein is collagen. Collagen occurs in fibrillar and non-fibrillar forms. In the latter, the Gly-X-Y collagen repeat sequence is interrupted by other sequences. The length and extent of these other sequences may affect the thermal stability of the protein. Single triple helical collagen molecules can be extracted by any of several methods. See, for example, Miller and Rhodes, "Preparation and and Characterization of the Different Types of Collagen" in Cunningham and Drederisksen (eds.), *Methods Enzymol.* 82, part A:33–62, 1982; Cheung et al., *J. Biol. Chem.* 258:7774–7778, 1983; Mayne and Zettergren, *Biochemistry* 19:4065–4072, 1980; Carmichael et al., *Biochim. Biophys. Acta* 491(1):177–192, 1977; Bishop et al., *Biochem. Biophys. Res. Comm.* 185:392–397, 1992; and U.S. Pat. No. 4,703,108. Gelation of collagen occurs when the individual molecules aggregate and form fibrils (Djabourov et al., *Biorheology* 30:191–205, 1993). Collagen remains soluble in acid at low temperature and ionic strength. The rate of gelation of collagen increases with increasing temperature to an optimum temperature that is dependent in part on the source species, type of collagen, protein concentration, pH, and ionic strength. Collagens from mammalian species typically gel within a range of about 25° C. to 37° C. For example, an aqueous solution of bovine fibrillar collagen (commercially available from Collagen Corporation, Fremont, Calif.) is adjusted to isotonicity and near-neutral pH (7.4±0.2). The resulting solution can be stored at 4°–6° C. for several hours. Gelation (fibrillogenesis) is initiated by warming the solution to 37° C. for at least about 60 minutes. The temperature range within which collagen gels are stable varies with the type of collagen and the species. The amounts of proline and hydroxyproline residues and their positions within the collagen molecules are primarily responsible for this variation in temperature stability. Variation is believed to have arisen in response to environmental factors such as habitat temperature and pressure (Har-El and Tanzer, *FASEB J.* 7:1115–1123, 1992). As described in more detail below, transglutaminase is added to the collagen solution prior to or during gelation, or may be applied to the surface after gelation is substantially complete. Thus, the methods and compositions comprising gelatin described below are representative of certain embodiments of the invention, and can be readily adapted for use with other temperature-sensitive gel-forming proteins.

Within certain embodiments of the invention, gelatin is prepared as an aqueous solution. It is preferred to dissolve gelatin in an aqueous solvent buffered at pH 5.5–9.0 and of low to moderate ionic strength (equivalent to about 1 to 1000 mM NaCl, preferably 100 to 150 mM NaCl). While salt is not required in the buffer, certain proteins are more soluble in the presence of salt, and near-physiological concentrations of salt are beneficial in compositions that are to be used within living organisms. Preferably the pH of the solution is about 6.0–8.0, more preferably about 7.4. A preferred aqueous solvent in this regard is phosphate buffered saline (PBS; 10 mM sodium phosphate pH 7.4, 120 mM NaCl, 2.7 mM KCl). Other suitable buffers include borate, phosphate, HEPES (N-[2-Hydroxyethyl]piperazine-N'-[2-ethanesulfonic acid]) and the like. The concentration of gelatin will be determined according to its intended use, but will generally be 20% or less by weight, more commonly 1%–10%. It is convenient to prepare a concentrated solution (e.g., a 10% stock solution) that can be diluted to the desired working concentration immediately prior to gelation and cross-linking. The gelatin is allowed to swell, typically for about two hours, then melted by raising the temperature to above the gel point of the solution, preferably to at least 32° C. up to 100° C. or more, more preferably to 32° C. to 60° C. Use of temperatures above 60° C. significantly increases the time required for gelling upon cooling of the solution. The solution can then be gelled, such as by allowing it to stand overnight at room temperature, and stored refrigerated until needed. If stored in the solid state, the gel is melted immediately before use by heating (typically to 37° C.) and diluted to the desired working concentration (commonly about 2% to 6.6% weight/volume). While not necessary for the realization of certain benefits of the invention, the solidification and re-melting of the solution has been found to improve the rate of gelation and may therefore reduce the amount of transglutaminase needed to obtain the desired degree of cross-linking. Large amounts of transglutaminase can cause deamidation, rather than cross-linking, of glutamine residues in the protein.

Transglutaminase is then added to the solution of gelatin in the sol state. Depending upon the transglutaminase used, the solution may also contain sufficient calcium (1–18 mM, preferably about 3 mM, as $CaCl_2$) for transglutaminase activity. Mammalian transglutaminases, including factor XIII, tissue transglutaminase, keratinocyte transglutaminase, epidermal transglutaminase, and prostate transglutaminase, require $Ca^{++}$ for activity, while others, including certain bacterial transglutaminases (see, e.g., European Patent Office Publication 0 379 606 A1; U.S. Pat. No. 5,420,025), do not require $Ca^{++}$. When using factor XIII zymogen as the transglutaminase, thrombin (0.1–10 U/ml, preferably about 1 U/ml) is included for activation of the factor XIII. Transglutaminases may also be pre-activated (e.g., factor XIIIa) or a tranglutaminase not requiring activation can be used (e.g., tissue transglutaminase or keratinocyte transglutaminase). The ratio of gelatin:transglutaminase will generally be within the range of 1320:1 to 20:1 by weight, preferably 528:1 to 66:1, more preferably 264:1 to 66:1. The concentration of transglutaminase within the solution will typically be from 0.125 mg/ml to 2.0 mg/ml, preferably at least 0.5 mg/ml, although the concentration can be adjusted to provide gels with low melting points or very high or low tensile strength. The solution is then incubated under conditions of time and temperature in which a like solution lacking transglutaminase will gel. Gelatin-transglutaminase solutions are incubated at from about 4° C. up to the gel point, preferably from 4° C. to 33° C., more preferably at a temperature of at least 20° C. up to about 32° C. Those skilled in the art will recognize that time to gel formation is a factor of temperature and protein concentration, and the actual time and temperature of incubation will be determined with consideration of all relevant parameters. For example, the critical gelation point for 4% (w/v) Type A gelatin is 29.1° C. (Michon et al., ibid.), and a 5% gelatin solution will gel in 260 minutes at 26° C.

Within an alternative embodiment of the invention, transglutaminase can be added to a composition of a temperature-sensitive gel-forming protein during or subsequent to gelation, in the latter case allowing the transglutaminase to diffuse into the gel. For example, an aqueous solution of transglutaminase is applied to the surface of a newly-formed collagen or gelatin gel and allowed to diffuse into the gel. The gel and transglutaminase are incubated under conditions conducive to gel formation for the protein used within the gel. For example, a factor XIII solution is applied to the surface of gelatin gel and incubation is carried out at below the melting point of the gelatin, preferably about 20° C. to 32° C. Diffusion time, and amount and concentration of transglutaminase can be adjusted to provide the desired depth of penetration and degree of cross-linking. This alternative method is particularly suited to cross-linking gels that are sufficiently thin to allow the tranglutaminase to diffuse throughout the gel; to produce thin, cross-linked membranes; or to harden surfaces of thicker gel products, including foodstuffs wherein a soft center surrounded by a harder coating is desired. Within one method for preparing thin membranes, after the desired degree of penetration and cross-linking has occured, the gel is heated to above the melting point of the non-cross-linked gel, and melted protein is separated from the remaining membrane.

Additional proteins can also be incorporated into gels of the present invention. It is known in the art that transglutaminases will catalyze the formation of bonds between a glutamine-containing peptide and a peptide containing an $\epsilon$-lysine amine. It is therefore possible to cross-link most proteins containing susceptible lysine or glutamine residues into a protein gel if the gel-forming protein contains a suitable complementary residue. Suitable additional proteins in this regard include fibronectin, vinculin, von Willebrand factor, laminin, fibrin, and various hormones and cytokines, including, for example, the AA, BB, and AB isoforms of platelet derived growth factor (PDGF), transforming growth factors $\alpha$ and $\beta$ (TGF-$\alpha$ and TGF-$\beta$), and acidic and basic fibroblast growth factors (aFGF and bFGF). Methods for preparing these proteins are known in the art. See, for example, Lynch et al., *Cell* 41:49–56, 1985; Chopek et al., *Biochemistry* 25:3146–3155, 1986; Obara et al., *Cell* 53:649–657, 1988; Asijee et al., *Biochim. Biophys. Acta* 954:303–308, 1988; Dufour et al., *EMBO J.* 7:2661–2671, 1988; Brubacher et al., *Exp. Cell Res.* 197:290–299, 1991; Brandenberg and Chiquet, *J. Cell Science* 108:3099–3108, 1995; U.S. Pat. Nos. 4,703,108; 4,801,542; 4,766,073; 4,902,782; 5,104,977; 5,155,214; and WIPO Publication WO 95/23868). Additional proteins are included in the gel in an amount not exceeding 50% by weight of the total gel protein. It is preferred that the amount of additional protein not exceed 10% by weight. It is particularly preferred that additional proteins, when included, be present at 1%–5% by weight, although for certain proteins and applications the content will be substantially less.

The gels of the present invention can also comprise amine-containing, non-proteinaceous compounds.

Examples of such compounds are the polyamines spermidine, cadaverine, and putrescine, which can provide attachment sites for cells; and bis-amine polyethylene glycol, which can be included to modify gel structure.

The gels of the present invention can be used in industrial and medical applications in place of conventional crosslinked and non-cross-linked gels. Such applications include photographic films, gelatin-containing foodstuffs, gelatin capsules (particularly microcapsules), drug delivery devices, and prosthetic devices. The enzymatically cross-linked gels of the present invention provide the advantages of uniformity and specific cross-linking in combination with high thermal stability, which permit use of the gels within new and expanded applications.

The methods of the present invention can be used in the preparation of photographic emulsions. Photographic emulsions are typically gelatin-based emulsions containing one or more of silver halide grains, dye-forming coupler compounds, ultraviolet absorbing materials, developing agents, etc. These compounds are added to the gelatin to form a mixture which is applied to a polymeric film base or paper surface in the sol state and allowed to gel and cross link. Surfaces can be coated with single or multiple layers of emulsion as desired. Methods for preparing photographic emulsions and applying them to surfaces are known in the art. See, for example, U.S. Pat. Nos. 3,607,345; 4,214,047; and 4,269,927, which are incorporated herein by reference in their entirety.

The methods of the present invention can also be used in the preparation of protein-containing food products, for example to improve the functional properties of proteinaceous foods. Within the present invention, transglutaminase is added to such foodstuffs as minced meat, fish paste, milk, gelatin, whey protein, soy protein, wheat protein, maize protein, egg albumin, rape seed protein, potato protein, and the like. The resulting mixture is incubated for a period of time sufficient for gelation to occur and for the transglutaminase to react with the substrate. Foodstuffs prepared in this manner exhibit increased water binding capacity, improved texture, improved thermal stability, and other advantages. The resulting alteration in the functional properties can be utilized to lower the fat content in the food product, because the crosslinked protein simulates properties associated with a higher fat content. The methods of the present invention are particularly useful in the preparation of food products rich in gelatin or collagen, such as gelatin desserts and collagen sausage casings.

The methods of the present invention can be used to prepare drug delivery vehicles such as microcapsules. For example, gelatin microcapsules can be prepared by complete coacervation (Thies, *Crit. Rev. Biomedical Engineering* 8: 335–383, 1982; incorporated herein by reference). Two oppositely charged polyelectrolytes (gelatins type A and B) are combined in an aqueous solution to form a coacervate which also includes the drug to be encapsulated. During gelation, the mixture is vigorously agitated to form small beads, which are cross-linked by transglutaminase as disclosed herein, making them relatively insoluble, yet biodegradable. In the alternative, microcapsules can be formed from organic/aqueous emulsions according to known methods and subsequently cross-linked. Microcapsules containing both peptidic and non-peptidic drugs can be prepared by this method. In a related embodiment, drugs containing amines, including proteins and peptides containing lysine residues, can be covalently bonded to microcapsules during the hardening process. Amine-containing substances can be added to the gel prior to or during cross-linking, whereby the amines become covalently bonded to glutamine residues in the gel-forming protein by the action of the transglutaminase. Microcapsules of this type can be used to provide localized or timed-release delivery of drugs. Drugs that can be delivered in this way include hirudin, glucagan, insulin, protamine, amphomycin, and bacitracin.

The gels of the present invention can also be used in prosthetic devices, for example to promote the adhesion of vascular endothelial cells seeded on prosthetic vascular grafts. Methods for seeding and sodding vascular grafts with endothelial cells are disclosed by, for example, Budd et al., *Br. J. Surg.* 76:1259–1261, 1989; Kaehler et al., *J. Vasc, Surg.* 9:535–541, 1989; Mosquera and Goldman, *Br. J. Surg.* 78:656–660, 1991; WIPO Publication WO 91/16009; and Rubens et al., U.S. Pat. No. 5,324,647. vascular endothelial cells attach and spread when their cell membrane integrins is contact and bind to matrix components such as fibronectin, laminin, and von Willebrand factor. In the case of fibronectin the N-terminus contains a transglutaminase substrate site that allows it to be cross-linked to a gelatin or collagen matrix. See Bockenstedt et al., *J. Clin. Invest.* 78:551–556, 1986. The C-terminal portion of fibronectin contains the ligand for binding to the a5b1 integrin. Properly oriented fibronectin will act as a tether for endothelial cells and could be used to reduce sluffing of seeded endothelial cells. Other proteins that provide contact points for cell attachment and/or migration and cytokines can also be included. Polyamines, such as spermidine, cadaverine, and putrescine can also be included to provide cell-attachment points.

Protein gels can be shaped by casting (forming the gel within a mold while in a plastic state) or by extruding during or after cross-linking to produce a fiber that can be woven. Additional compounds can be incorporated into or onto such gels. For example, amine-containing compounds can be bound to a surface of a prosthetic material to provide a transglutaminase substrate site. Methods of binding include treatment with a strong oxidant, such as potassium permanganate, nitric acid, dichromates, or peroxides; cross-linking; and adsorption.

Cross-linked gels of the present invention can be used in surgical applications where non-cross-linked gels are currently used, such as in neural reconnective surgery to prevent adhesions. Polymeric gels of this type are known in the art (e.g., ADCON®, semisynthetic carbohydrate polymeric gels, produced by Gliatech Inc., Cleveland, Ohio). Cross-linking stabilizes the gel, increasing its residence time.

Enzymatically cross-linked gels are particularly well suited for in vivo uses in view of the protease resistance of stabilized helices and the improved thermal stability of the gels. Gels having a melting point of 37° C. or above can be prepared, with the actual melting point depending on the degree of cross-linking. It is thus possible to prepare gels that are stable at, for example, 45° C., 65° C., or 100° C.

The invention is further illustrated by the following non-limiting examples.

EXAMPLES

Example 1

All viscosity measurements were taken at 37° C. in a jacketed Brookfield DV III cone and plate viscometer with a cp40 one (Brookfield Engineering Labs, Stoughton, Mass.).

Human factor XIII $A_2$ dimer was produced in *S. cerevisiae* and stored as a lyophilized powder containing 13.2 mg factor XIII, 0.66 $\mu$Moles EDTA, 6.60 $\mu$Moles glycine, and 0.13 grams sucrose. Prior to use, the lyophilized material was dissolved in 1 ml of distilled water.

Calf skin Type A gelatin, high Bloom strength (Ferrosan International A/S, Soeborg, Denmark) was dissolved in Tris-buffered saline (TBS: 25 mM Tris pH 7.4, 120 mM NaCl, 0.2% $NaN_3$) containing 3 mm $CaCl_2$. A 10% w/v stock solution was allowed to swell at room temperature for two hours. The gelatin was dissolved by heating at 37° C., and the solution was allowed to gel overnight at 4° C.

The 10% w/v gelatin stock was melted at 37° C. and diluted to 4% w/v with TBS+$CaCl_2$, and 1-ml aliquots were dispensed into 13 100-mm plugged test tubes. The experiment was initiated by adding 1 mg recombinant human factor XIII and 10 units bovine thrombin (Enzyme Research Laboratories, West Bend, Ind.) to each tube. The tubes were incubated at 27° C. to allow gelling of the solution, and viscosity measurements were taken at intervals until the viscosity exceeded the range of the instrument (290 minutes). For each time point during gelation an aliquot was incubated for five minutes at 37° C., and a second aliquot was incubated at 100° C. The viscosities of both aliquots were then measured at 37° C. after an equilibration period of five minutes. Control samples containing no factor XIII were melted and measured at 37° C. only.

As shown in FIG. 1, the viscosity of the control containing no factor XIII (>) increased only slightly over the entire course of the experiment. Samples containing factor XIII incubated at 100° C. (•, Δ) exhibited a slow increase in viscosity for about 250 minutes, then viscosity increased exponentially until going off the scale after the 290 minute time point. Factor XIII- containing samples incubated at 37° C. (■) showed an almost immediate increase in viscosity, which after only 60 minutes reached a point equivalent to the viscosity of the 270 minute time point in the samples incubated at 100° C.

The differences in viscosity between the 37° C. and 100° C. samples are interpreted as indicating a loss of structure at the higher temperature for reaction times shorter than 250 minutes. The small but continuous increase in the viscosity of the 100° C. samples suggests that some cross-linking is occurring at times below 250 minutes. The increase in viscosity seen below 250 minutes in the 37° C. samples is probably due to partial stabilization of the gel structure by a few covalent bonds. It has been reported by Michon et al. (*Rheol. Acta* 32: 94–103, 1993) that the gel point of 4% gelatin at 27° C. is greater than or equal to 250 minutes. Earlier experiments (Bishop et al., *Biochemistry* 29:1861–1869, 1990) showed that activation of factor XIII by thrombin (10 U thrombin/1 mg factor XIII) is complete in 15 minutes. The long lag period for the increase in viscosity is believed to reflect the formation of adhesion zones during gelation, which are essential for the occurrence of factor XIII—catalyzed cross-linking.

Example 2

A 6.6% w/v gelatin mixture in 100 mM NaCl was allowed to swell for three hours, then dissolved at 60° C. 20 ml of the 6.6% gelatin solution was combined with 1 ml $H_2O$ containing 146 mg EDC (1-ethyl-3-[3-(dimethylamino)propyl] carbodiimide) adjusted to pH 5.0 with NaOH. Samples were incubated for two hours at 22° C. to allow cross-linking to occur.

Tensile strength (load at break) was determined using an Instron (Canton, Mass.) Model 4500 materials tester. Aliquots of the gel were prepared in 2 cm diameter×0.75 mm jigs for tensile strength testing. The jigs were designed so that axial displacement of the upper and lower members occurred without lateral displacement, thereby ensuring that upper and lower surfaces remained parallel during testing. Aluminum foil was bonded to the bonding surfaces of the jig to provide a substrate for the test sample. Plastic shims of precise thickness were placed between the upper and lower jig mimbers to control guage length. Thicker guage lengths were found to reduce susceptibility to imperfections in the surface of the aluminum foil substrate or misalignments of the jig members. The lower jig member was secured in a base clamp, and the upper member was secured by a clamp mounted to the transducer by means of a universal joint. The transducer was moved upwards, measuring force and distance until a break occurred. All measurements were recorded automatically. Results are shown in Table 1.

TABLE 1

| Sample (n = 6) | Load at Break (kg/3.14 cm²) |
|---|---|
| Control | 2.050 ± 0.540 |
| +EDC | 3.214 ± 0.300 |

Example 3

The effects of cross-linking protamine sulfate and fibronectin into gelatin were investigated. All samples contained a final concentration of 4% gelatin in 25 mM Tris pH 7.4, 100 mM NaCl, 3 mM $CaCl_2$, 0.2% $NaN_3$. Control samples contained gelatin only, gelatin plus 0.4 mg/ml human fibronectin (obtained from Alpha Therapeutics, Los Angeles, Calif. and chromatographically purified on DEAE resin to remove albumin), or gelatin plus 0.4 mg/ml protamine sulfate (Salmon grade X, Sigma Chemical Co., St. Louis, Mo.). Experimental samples further contained 2 mg/ml recombinant human factor XIII. Factor XIII was activated at the start of the experiment by the addition of 1 unit/ml of bovine thrombin. The samples were incubated at 37° C. for one hour and allowed to gel for 2 hours. Compressive testing of the samples was performed with an Instron Model 4500 materials tester quipped with a 5 mm probe. The probe was pushed into a 1.5 mm diameter contained gelatin sample until a break as recorded. Results are shown in Table 2.

TABLE 2

| Sample (n = 5) | Max. Load (kg/0.196 cm²) | Energy to Break (kg/mm/0.196 cm²) |
|---|---|---|
| Control | 0.054 ± 0.021 | 0.176 ± 0.019 |
| +FXIII | 0.077 ± 0.016 | 0.319 ± 0.042 |
| +FN | 0.065 ± 0.098 | 0.125 ± 0.030 |
| +FN, +FXIII | 0.087 ± 0.026 | 0.620 ± 0.189 |
| +Prot. | 0.063 ± 0.019 | 0.174 ± 0.025 |
| +Prot., +FXIII | 0.063 ± 0.010 | 0.166 ± 0.028 |

FXIII, factor XIII; FN, fibronectin; Prot., protamine sulfate

The maximum load at breaking was not substantially different for between control and factor XIII samples, but the energy to break for the +FN, +FXIII sample was greater than 2.4 times that of the control.

Example 4

Gelatin (10% by weight) in 350 ml of 25 mM Tris pH 7.4, 100 mM NaCl, 3 mM $CaCl_2$ was allowed to swell for two hours at room temperature and then dissolved by incubating at 37° C. in a water bath. The solution was returned to room temperature for at least two hours to allow it to gel. Viscosity of the gel, as determined using a cone and plate viscometer (Brookfield), was 6 cp. The gel was remelted at 37° C. and allowed to gel again, after which the viscosity was determined to be 12 cp.

Example 5

330 ml of 10% gelatin in 25 mM Tris pH 7.4, 100 mM NaCl, 3 mM $CaCl_2$, 0.2% $NaN_3$ was allowed to swell for two hours at room temperature and then dissolved at 37° C. in a water bath. The solution was gelled at room temperature in a water bath and remelted at 37° C. The solution was diluted to 6.6% gelatin by adding 149.1 ml of 25 mM Tris pH 7.4, 100 mM NaCl, 3 mM $CaCl_2$, 0.2% $NaN_3$. To 239.6 ml of the diluted solution was added 18.9 ml of recombinant human factor XIII (13.2 mg/ml in glycine/EDTA/sucrose storage buffer) or 18.9 ml of buffer alone, plus 1.0 ml of bovine thrombin (500 U/ml in 25 mM Tris, pH 7.4). Each sample was divided into six 40 g aliqouts, which were placed in 50 ml beakers sealed with Parafilm and incubated at 21° C. for 20 hours.

The gels were placed in an Instron (Canton, Mass.) Model 4500 materials tester. A 12 mm probe coupled to a 100N cell was run into the gel at 17 mm/minute. Measurements were continued until the gel failed. All control gels had an initial partial failure followed by a complete failure. The initial failure was not observed in the factor XIII cross-linked gels. Test results are shown in Table 3.

TABLE 3

| Sample | Load at Break (kg/1.13 $cm^2$) | Young's Modulus (kg/$cm^2$/mm) |
|---|---|---|
| 6.6% gelatin | 0.557 ± 0.112 | 0.046 ± 0.004 |
| 6.6% gelatin + factor XIII | 1.469 ± 0.183 | 0.159 ± 0.030 |

Example 6

A 4% gelatin solution in 25 mM Tris pH 7.4, 100 mM NaCl, 3 mM $CaCl_2$, 0.2% $NaN_3$ was prepared as described in Example 5. Samples were prepared in 2 cm diameter X 0.75 mm tensile jigs. Factor XIII was added to test samples, and all samples were incubated for 20 hours at room temperature. Tensile strength was determined essentially as described in Example 2. Results are shown in Table 4.

TABLE 4

| Sample (n = 5) | Load at Break (kg/3.14 $cm^2$) |
|---|---|
| control | 1.192 ± 0.305 |
| +factor XIII | 2.196 ± 0.550 |

Figure 2:
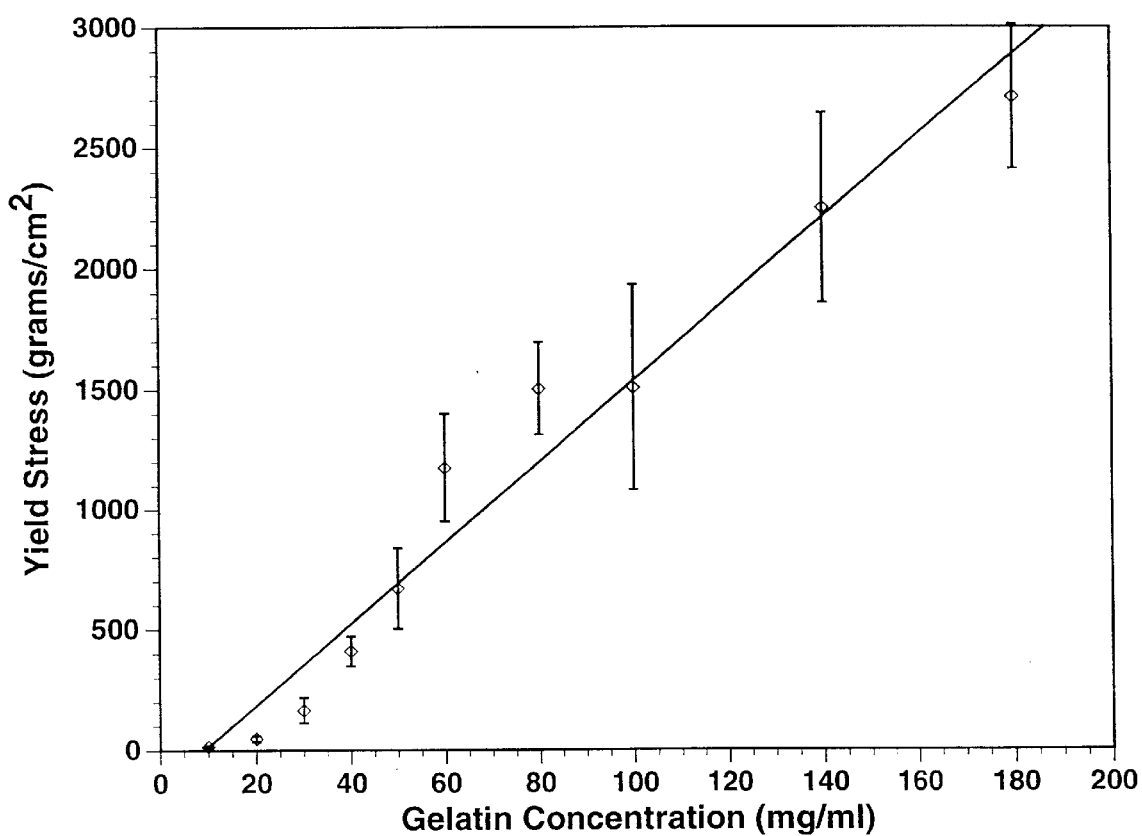
FIG. 2 illustrates the relationship between gelatin concentration and tensile strength.

All breaks appeared to be adhesive (the gel did not break internally but pulled away from the aluminum foil that was bonded to the jig) in both controls and factor XIII-containing samples. Because a linear relationship exists between gelatin concentration and strength (FIG. 2), results in Table 4 can be extrapolated to 1.97 and 3.62 kg/3.14 $cm^2$ for non-cross-linked and cross-linked 6.6% gels, respectively. These values are comparable to those for EDC cross-linked gels (Example 2).

Example 7

The melting temperatures of gels prepared using various concentrations of factor XIII were determined. Type A gelatin (Ferrosan International A/S) was dissolved in 25 mM Tris pH 7.4, 100 mM NaCl, 3 mM $CaCl_2$ to a concentration of 6.6%. The indicated amounts of factor XIII and bovine thrombin (1 U/ml) were added to the gelatin solution, and the mixture was incubated at 37° C. for 15 minutes. The gelatin was then allowed to gel and cross-link at room temperature for 18 hours. Melting temperatures were determined by observation of 1 ml of gelatin after 30 minutes at the specified temperature.

Results are shown in Table 5.

TABLE 5

| Factor XIII ($\mu$g/ml) | Melting Point |
|---|---|
| 0 | 27–37° C. |
| 62 | 27–37° C. |
| 125 | 37–45° C. |
| 188 | 37–45° C. |
| 250 | 45–65° C. |
| 375 | 65–95° C. |
| 500 | >100° C. |
| 1000 | >100° C. |

From the foregoing, it will be appreciated that, although specific embodiments of the invention have been described herein for purposes of illustration, various modifications may be made without deviating from the spirit and scope of the invention. For example, the physical and chemical characteristics of gels can be varied as required for particular pharmaceutical or industrial applications. Accordingly, the invention is not limited except as by the appended claims.

We claim:

1. A method of preparing a cross-linked protein gel comprising:

adding a factor XIII transglutaminase to a composition containing gelatin, while the gelatin is in a sol state at or below about 37° C. so as to form a transglutaminase and gelatin mixture; and incubating said mixture at a temperature at which the gelatin undergoes gelation, wherein a cross-linked gelatin gel is formed by cross-linking of the gelatin by the transglutaminase.

2. A method according to claim 1 wherein said composition is an aqueous solution.

3. A method according to claim 1 wherein said composition is a gel.

4. The method of claim 1 wherein said composition further comprises one or more additional proteins selected from the group consisting of fibronectin, von Willebrand factor, vinculin, and laminin.

5. The method of claim 1 wherein said composition further comprises a cytokine or a hormone.

6. A method of preparing a cross-linked protein gel comprising:

forming an aqueous solution containing gelatin; and adding a factor XIII transglutaminase to said solution in an amount sufficient to catalyze cross-linking of the gelatin; and incubating said transglutaminase and said solution under conditions of time and temperature at which the gelatin undergoes gelation, wherein a cross-linked gelatin gel is formed by cross-linking of the gelatin by the transglutaminase.

7. The method of claim 6 wherein said aqueous solution is subjected to at least one cycle of gelation and melting before the addition of said transglutaminase.

8. The method of claim 7 wherein the transglutaminase concentration is from 0.125 mg/ml to 2.0 mg/ml.

9. The method of claim 6 wherein said transglutaminase-containing solution is incubated at a temperature of from 4° C. to 33° C.

10. The method of claim 6 wherein the gelatin concentration is from 1% to 10% by weight and said transglutaminase-containing solution is incubated at a temperature of from 20° C. to 32° C.

11. The method of claim 6 wherein said gelatin and factor XIII transglutaminase are present in a mass ratio from 528:1 to 66:1.

12. The method of claim 6 wherein said transglutaminase-containing solution further comprises one or more additional proteins selected from the group consisting of fibronectin, von Willebrand factor, vinculin, and laminin.

13. The method of claim 12 wherein said one or more additional proteins is present in said transglutaminase-containing solution in an amount not exceeding 10% by weight of total protein in said gel.

14. The method of claim 6 wherein said transglutaminase-containing solution further comprises a cytokine or a hormone.

15. A method of preparing a cross-linked protein gel comprising:

adding a factor XIII transglutaminase to a temperature sensitive protein gel containing gelatin, whereby said transglutaminase diffuses into the gel and catalyzes cross-linking of the gelatin.

16. A cross-linked gelatin gel prepared by the method of claim 1.

17. The cross-linked gel of claim 16, further comprising one or more additional proteins selected from the group consisting of fibronectin, von Willebrand factor, and laminin, and vinculin.

18. The cross-linked gel of claim 17, wherein said one or more additional proteins is present in said transglutaminase-containing solution in an amount not exceeding 10% by weight of total protein in said gel.

19. The cross-linked gel of claim 16, further comprising a cytokine or a hormone.

20. The cross-linked gel of claim 16 which is coated on a polymeric or paper support.

21. The cross-linked gel of claim 20 further comprising silver halide grains.

22. The cross-linked gel of claim 20 further comprising a dye-forming coupler compound.

23. The cross-linked gel of claim 16 which is in the form of a microcapsule.

24. A pharmaceutical composition comprising a vehicle and an amine-containing drug, wherein said vehicle comprises a cross-linked gelatin gel prepared by the method of claim 1, and wherein said drug is covalently bonded to said gel.

25. A method of preparing a cross-linked protein gel of claim 1, wherein the said mixture is incubated at a temperature from about 37° C. and decreased to about 4° C.

26. A method of preparing a cross-linked protein gel of claim 1, wherein the factor XIII transglutaminase and gelatin mixture is incubated at a temperature from about 37° C. and decreased to about room temperature.

27. The cross linked gel of claim 16, wherein the cross-linked gelatin gel has a Tm of greater than about 65° C.

28. The cross linked gel of claim 16, wherein the cross-linked gelatin gel has a Tm of greater than about 100° C.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( D ) TOPOLOGY: linear ( x i ) SEQUENCE DESCRIPTION: SEQ ID NO:1:

Leu  Ser  Gln  Ser  Lys
   1                    5